US011480692B2

(12) United States Patent
Casse et al.

(10) Patent No.: US 11,480,692 B2
(45) Date of Patent: Oct. 25, 2022

(54) PHANTOM

(71) Applicant: THE UNIVERSITY OF LIVERPOOL, Liverpool (GB)

(72) Inventors: Gianluigi Casse, Liverpool (GB); Jonathan Taylor, Liverpool (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 1 day.

(21) Appl. No.: 16/483,218

(22) PCT Filed: Feb. 5, 2018

(86) PCT No.: PCT/GB2018/050323
§ 371 (c)(1),
(2) Date: Aug. 2, 2019

(87) PCT Pub. No.: WO2018/142163
PCT Pub. Date: Aug. 9, 2018

(65) Prior Publication Data
US 2019/0369268 A1    Dec. 5, 2019

(30) Foreign Application Priority Data

Feb. 3, 2017 (GB) ..................... 1701853
Feb. 8, 2017 (GB) ..................... 1702089

(51) Int. Cl.
*G01T 1/16* (2006.01)
*G01T 1/29* (2006.01)
(Continued)

(52) U.S. Cl.
CPC .............. *G01T 1/16* (2013.01); *G01T 1/29* (2013.01); *A61B 6/583* (2013.01); *A61N 2005/1076* (2013.01); *A61N 2005/1087* (2013.01)

(58) Field of Classification Search
CPC .. G01T 1/16; G01T 1/29; A61B 6/583; A61N 2005/1076; A61N 2005/1087
See application file for complete search history.

(56) References Cited

U.S. PATENT DOCUMENTS 3,031,575 A * 4/1962 Gevantman ............... G01T 1/04
                                                    250/252.1
5,273,435 A * 12/1993 Jacobson .............. G09B 23/286
                                                    434/262
(Continued)

FOREIGN PATENT DOCUMENTS

EP      2634601 A2    9/2013
JP    2014054438 A    3/2014
(Continued)

*Primary Examiner* — Blake C Riddick
(74) *Attorney, Agent, or Firm* — Lando & Anastasi, LLP (57) ABSTRACT

Embodiments of the present invention provide a phantom and radiation detection system (100) comprising a vessel for containing a tissue equivalent liquid and adapted to pass a beam of test radiation into the vessel (110), a detector (140) adapted to determine the intensity of the beam of test radiation, the detector (140) being supported within the vessel (110) and movable therein along an expected path of the beam of test radiation, wherein the detector (140) is a 2-dimensional detector adapted to determine the spatial intensity and energy deposition of the beam.

11 Claims, 9 Drawing Sheets

(51) Int. Cl.
*A61B 6/00* (2006.01)
*A61N 5/10* (2006.01)

(56) References Cited

U.S. PATENT DOCUMENTS

| | | | |
|---|---|---|---|
| 5,621,214 A | 4/1997 | Sofield | |
| 7,193,220 B1* | 3/2007 | Navarro | G01T 1/169 |
| | | | 250/252.1 |
| 7,268,358 B2 | 9/2007 | Ma et al. | |
| 8,632,448 B1 | 1/2014 | Schulte et al. | |
| 9,207,193 B2 | 12/2015 | Censor et al. | |
| 2006/0239403 A1* | 10/2006 | Udpa | G01N 23/046 |
| | | | 378/62 |
| 2006/0239404 A1* | 10/2006 | Udpa | A61N 5/10 |
| | | | 378/62 |
| 2007/0223654 A1* | 9/2007 | Aufrichtig | A61B 6/037 |
| | | | 378/116 |
| 2008/0217561 A1* | 9/2008 | Mackie | A61N 5/1075 |
| | | | 250/492.3 |
| 2009/0057562 A1* | 3/2009 | Heijne | G01T 1/026 |
| | | | 250/370.07 |
| 2010/0041005 A1* | 2/2010 | Campbell | G09B 23/28 |
| | | | 434/267 |
| 2010/0202001 A1* | 8/2010 | Miller | G16H 30/20 |
| | | | 358/1.9 |
| 2011/0027853 A1* | 2/2011 | Bert | A61N 5/1048 |
| | | | 435/173.1 |
| 2012/0168630 A1* | 7/2012 | Beddar | G01T 1/04 |
| | | | 250/362 |
| 2012/0228493 A1 | 9/2012 | Gottschalk et al. | |
| 2013/0099119 A1* | 4/2013 | Derat | G01R 29/08 |
| | | | 250/336.1 |
| 2013/0287170 A1 | 10/2013 | Ebstein | |
| 2013/0292580 A1* | 11/2013 | Schubert | A61N 5/1048 |
| | | | 250/395 |
| 2015/0071408 A1 | 3/2015 | Ebstein | |
| 2015/0196779 A1* | 7/2015 | Tonner | A61N 5/1049 |
| | | | 600/1 |
| 2015/0306427 A1* | 10/2015 | Hirasawa | G01T 1/204 |
| | | | 250/363.08 |
| 2015/0327834 A1* | 11/2015 | Hoshino | A61B 6/5217 |
| | | | 378/207 |
| 2016/0103228 A1 | 4/2016 | Koltermann | |
| 2016/0133159 A1* | 5/2016 | Saloux | A61B 6/583 |
| | | | 73/866.4 |
| 2016/0135765 A1* | 5/2016 | Vigdor | G01T 1/169 |
| | | | 250/366 |
| 2019/0388054 A1* | 12/2019 | Qiu | A61B 6/502 |

FOREIGN PATENT DOCUMENTS

| | | |
|---|---|---|
| WO | 2015189601 A1 | 12/2015 |
| WO | 2016007599 A1 | 1/2016 |
| WO | 2016008901 A1 | 1/2016 |
| WO | 2018142163 A1 | 8/2018 |

\* cited by examiner

PHANTOM

CROSS-REFERENCE TO RELATED APPLICATIONS

This application is a U.S. National Stage Application under 35 U.S.C. § 371 of International Application No. PCT/GB2018/050323, filed Feb. 5, 2018, entitled "PHANTOM," which claims priority to application no. GB 1702089.2 filed Feb. 8, 2017, and application no. GB 1701853.2, filed Feb. 3, 2017, each of which are herein incorporated by reference.

The present invention relates to a phantom.

BACKGROUND

A phantom, which may also be referred to as an imaging phantom or tissue equivalent phantom, is an object that is used to characterise radiation. Phantoms are usually used in medical science to mimic the response of a human body, or parts thereof, such as human organs and tissues to various stimuli, in order to prevent a living subject from being exposed to any unnecessary risk. Phantoms may be used to test responses to various kinds of radiation, including X-ray, gamma and charged particle (e.g. electrons, ions, protons) radiation. In this way, the energy deposited by the radiation is measured in order to plan treatment for individual patients.

Phantoms may be used to measure the energy deposition as a function of penetration depth in a number of applications.

It is desirable for the phantom to accurately mimic the response of a human body and to measure the radiation and its energy deposition as accurately as possible.

It is an object of embodiments of the invention to at least mitigate one or more of the problems of the prior art.

BRIEF SUMMARY OF THE DISCLOSURE

Aspects provide a phantom and system as set forth in the appended claims.

BRIEF DESCRIPTION OF THE DRAWINGS

Embodiments of the invention are further described hereinafter with reference to the accompanying drawings, in which:

FIGS. 12(a) and (b) are front and side cross-section views respectively of a flange for use in supporting a window in the vessel;

FIGS. 13(a) and (b) are front and side cross-section views respectively is an illustration of a window and front wall of the vessel;

FIGS. 15(a) and (b) are perspective and exploded perspective views respectively of a portion of a support assembly for supporting two detectors in the vessel.

DETAILED DESCRIPTION

Figure 1:
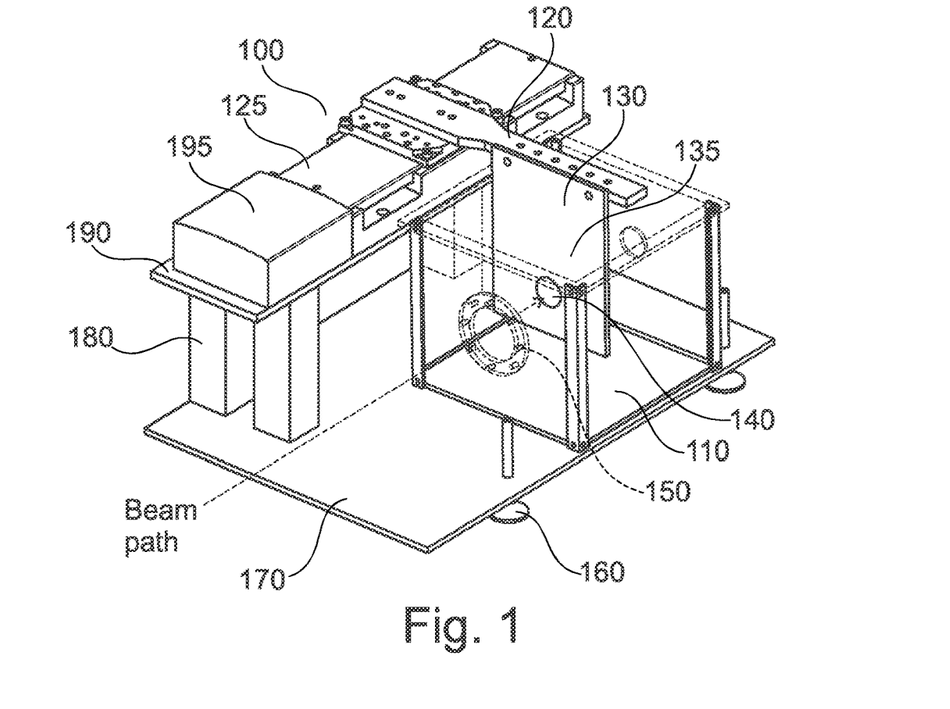
FIG. 1 is an isometric view of an example phantom and support assembly according to the disclosure.
Figure 2:
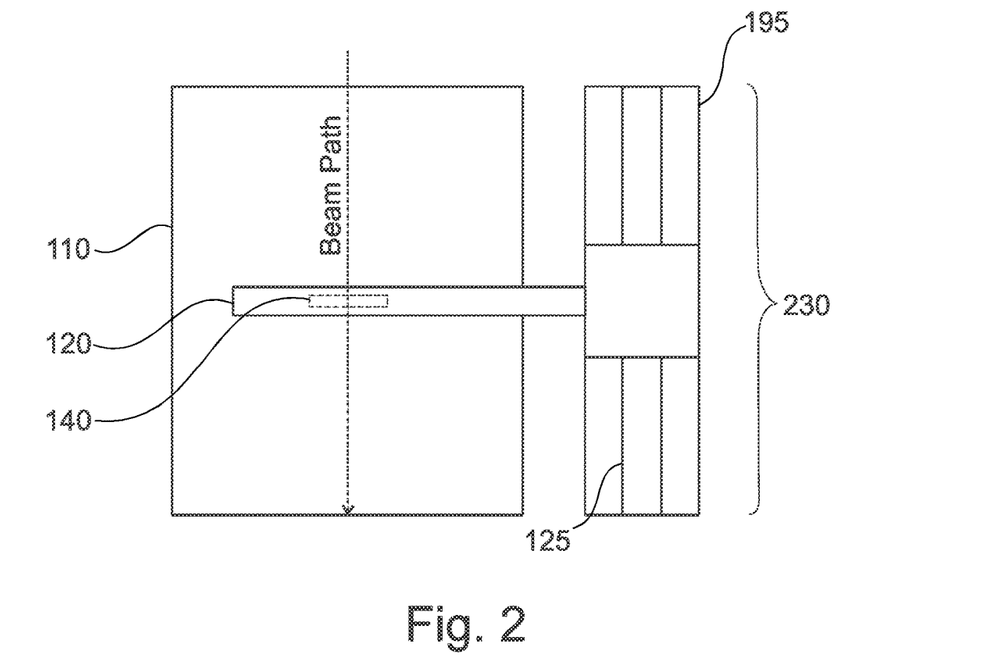
FIG. 2 is a simplified top view of a phantom and support assembly according to the disclosure.
Figure 3:
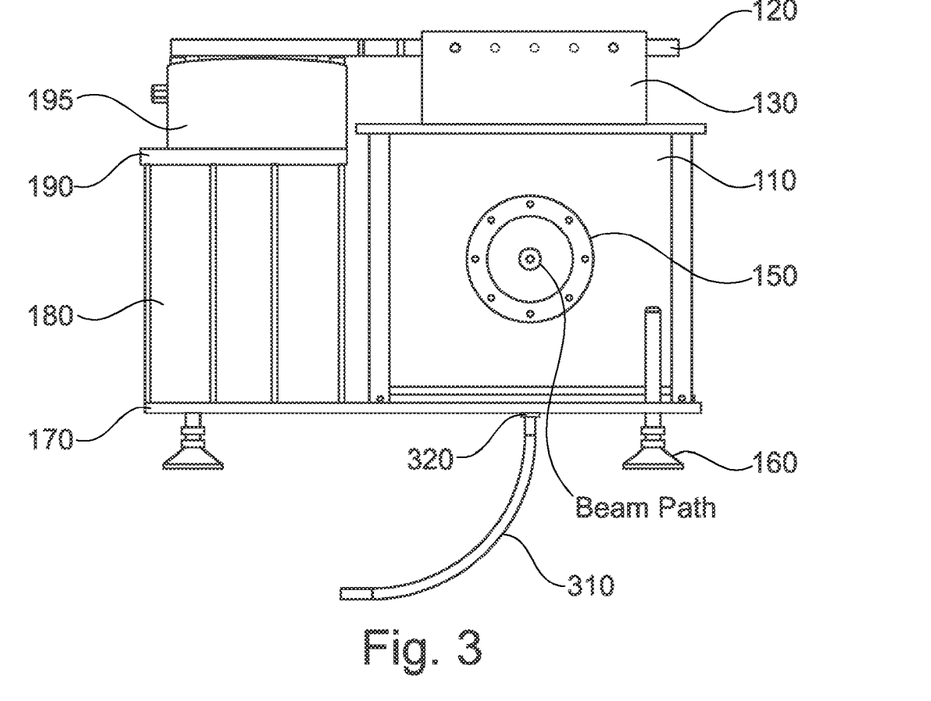
FIG. 3 is a front view of the phantom and support assembly shown in FIG. 1.

Referring initially to FIGS. 1, 2 and 3, there is shown a phantom, indicated generally by a reference numeral 100. Such a phantom 100 may be used to determine the intensity, the energy deposition and the penetration depth of a beam of test radiation, such as a proton beam. The phantom 100 comprises a vessel 110 for containing a tissue equivalent liquid and a detector 140. The detector 140 may be suitable for determining the intensity, the energy or both of the beam of test radiation. The detector 140 is a 2-dimensional detector adapted to determine the spatial intensity and energy of the beam cross section, also referred to as the beam spot, and is movable within the vessel 110 along the path of the beam of test radiation. The detector 140 is supported within the vessel 110 by a support assembly.

The vessel 110 is a cuboid tank with an open top. The walls of the vessel 110 are adapted to pass a beam of test radiation into the tissue equivalent liquid. The walls of the vessel 110 may be made out of Plexiglas or other suitable material. Preferably, the walls are made of a transparent material so that users may see inside. The walls of the vessel 110 may be provided with a noise suppression coating or layer so as to reduce the effects of stray radiation on the measurements. One wall of the vessel may include a window 150 adapted to allow the beam of test radiation to pass into the vessel. The window 150 may be made out of polymethyl methacrylate (PMMA) or a resin material such as that referred to as "solid water". Typically, the window material will have density close to that of water. The window material should be suitable to be machined flat to a thickness of in the region of 1 mm to 3 mm while still being strong enough to withstand the pressure in the vessel without distortion. It will be apparent that other suitable materials may be used. Advantageously, the window 150 may be thinner than the walls of the vessel 110. In this way, any distortion to the beam caused by the window is reduced. Further, it is possible to position the detector as close as possible to the location at which the beam enters the vessel. The window 150 may be between 1 mm and 2 mm thick and in a preferred arrangement is 1.3 mm thick. The window may be fitted in a flange that fits within a suitable hole in the front wall of the vessel.

FIG. 3 shows a drainage tube 310 and a vacuum port 320 underneath the vessel 110. The drainage tube 310 and the vacuum port 320 are used for drainage of the tissue equivalent liquid from the vessel 110.

In use, the vessel 110 is filled with a tissue equivalent liquid, for example water. The water may be deionized water as, advantageously, this reduces interference or errors caused by ions in the water. The detector 140 is supported within the vessel 110 and submerged in the tissue equivalent liquid. The tissue equivalent liquid is present in order to interact with the beam of test radiation, and bring it to an equilibrium within the vessel 110. The beam of test radiation passes into the vessel 110 through the window 150. Typically, the radiation source is arranged to direct the beam of test radiation along a substantially horizontal expected path in the vessel. The detector 140 is arranged such that its detecting surface is substantially orthogonal to the expected path of the test beam. The beam impinges on the detector 140 and its intensity is spatially determined. The detector 140 determines the intensity and/or energy of the beam of test radiation in at least two dimensions simultaneously. The detector 140 may be a silicon based detector. The detector 140 may be a multi-channel detector. The detector 140 may be a pixel detector. The detector 140 may be a high granularity pixel detector, and may take the form of a hybrid pixel detector or a monolithic pixel detector.

Given that the pixel detector provides detection in two dimensions and is movable in a third dimension, it will be understood that the detector may be considered as a providing voxel-type analysis of the radiation. The expected path is chosen to allow the test beam of radiation to propagate into the vessel and towards the detector. In a cuboid vessel, the expected path for the test beam of radiation may typically be parallel to the sides and base of the vessel. The radiation may typically be a beam of charged particles, for example protons. The radiation may be a carbon ion beam or other suitable charged particle beam.

The detector 140 is supported within the vessel in such a way that it may be positioned along the expected path of radiation propagating in the tissue equivalent fluid within the vessel 110. Measuring the spatial intensity of the radiation beam in at least two dimensions, perpendicular to the expected path simultaneously, and moving along the expected path, allows the intensity and energy deposition of the radiation to be precisely spatially measured in three dimensions. Thus the range of the radiation, and the position of its Bragg peak—the peak in energy deposition just before a particle is stopped by matter—may be calculated, among other things.

Precise knowledge of the Bragg peak and range of the charged particle beam in three dimensions allows predetermined areas to be targeted to receive the maximal dosage from the beam. The radiation will deliver a relatively small dose to matter it interacts with before the peak, and the dose falls off rapidly after the peak. This means that in cancer radiotherapy, a patient may have their tumour targeted by radiation by arranging that the Bragg peak of the beam is located within the tumour, with a smaller dose being delivered to the surrounding healthy tissues.

The presence of a detector that may spatially determine the intensity of the radiation in two dimensions simultaneously allows a more complete view of the Bragg peak, allowing the user to determine if the beam of radiation is homogeneous in both lateral dimensions. Furthermore, as the beam of test radiation scatters in all directions, spatially determining the intensity of the test radiation in only one dimension at a time would underestimate the total intensity of the test radiation at any given time.

The support assembly is arranged next to the vessel 110, and is arranged to provide support to the detector within the vessel. The support assembly comprises a linear stage 125 arranged parallel to the expected path. An extension arm 120 extends out from the linear stage 125 over the vessel 110, perpendicular thereto. The support assembly further comprises a base 170, having feet 160. The base 170 supports legs 180, and the vessel 110. The legs 180 support a platform 190. The linear stage 125 runs along the length of a track 195, which is set on the platform 190. The linear stage 125 may be motorised or manually driven to allow the position of the detector 140 along the beam to be adjusted in use with high precision.

The extension arm 120 is connected to a tongue 130 comprising a target area 135. The detector 140 is mounted on the target area 135 such that it lies on the expected path of the radiation and perpendicular thereto. In this way, the detector 140 is moveable along the expected path with high precision. Preferably the tongue 130 is formed from a stiff material so as to prevent bending when moving in the tissue equivalent liquid. This allows the exact distance in the water between the detector 140 and the window 150 that the radiation travels to be known. In a preferred example, the tongue 130 may be made out of carbon fibre but it will be apparent that other materials may be used. It will be understood that the detector 140 may be supported within the vessel 110 by other means that allow the detector be held in the path of the radiation beam and moved along the path with high precision such that its distance from the wall of the vessel, i.e. the distance along the path of the beam, can be known to high degree of accuracy. In this way, materials having a high degree of stiffness are preferred so as to substantially eliminate any flexing.

The linear stage may provide for the extension arm 120 to be moved along the track 125 in increments. The size of the increments may be adjusted and may be chosen depending on the desired results. In a preferred method of operation, increments of 1 µm are used, however it will be understood that other increment sizes may be used. By using smaller increments, a highly detailed scan is obtained, however, a complete scan may take longer to complete. Therefore, it will be understood that the time for the scan may be reduced by increasing the size of the increments, but resulting in a loss of depth-wise granularity in the results.

Figure 9:
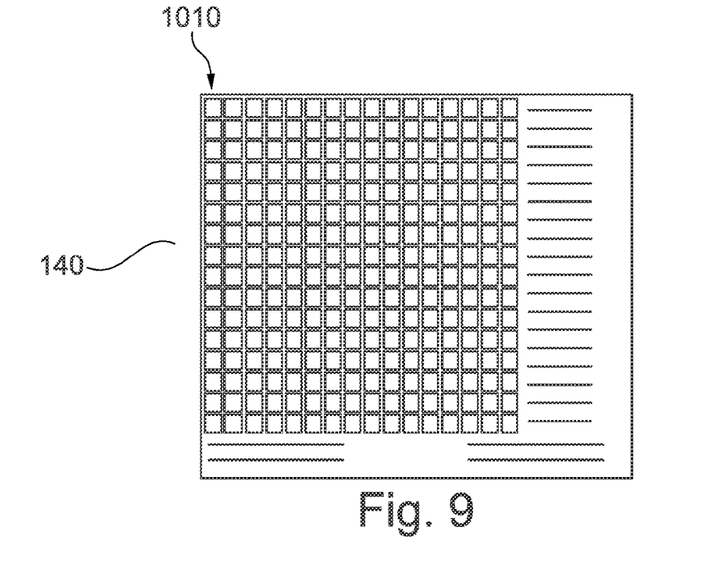
FIG. 9 is a block diagram of an example detector for use in the phantom.

Referring now to FIG. 9, there is shown a simplified representation of an example detector for use in the phantom, indicated generally by the reference numeral 140. The detector comprises an array of individual sensors 110, each considered as a single pixel. The array comprises a plurality of parallel rows of sensors. The number of rows and columns within the array of the detector is variable, represented by the dotted lines, depending on the size of the overall matrix and individual pixels.

The pixels of the detector 140 may be square or rectangular, or other suitable shape, with typical sizes of 50×50 µm² or 50×250 µm², but other sizes may be used. The size of the full detector may be 2×2 cm² or other sizes. The detector 140 may measure up to 10×10 cm² or larger. Using smaller pixel sizes provides greater spatial resolution but also generates more channels to read out and increased data thus data increasing cost and complexity of a readout chain of the detector 140.

Figure 10:
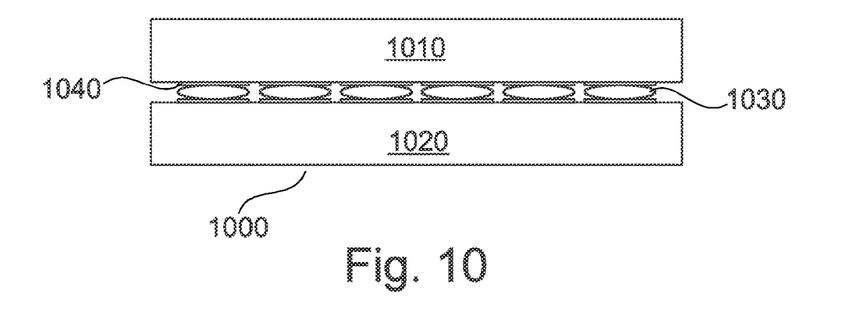
FIG. 10 is a simplified illustration of an example of a hybrid detector for use in the phantom.

Referring to FIG. 10, there is shown an example of a type of detector that may be used as part of the phantom 100. FIG. 10 shows a vertical cross-section of a hybrid pixel array 2-D detector 1000, with individual pixels 1040 formed by a combination of two chips. A sensor chip 1010 comprises an array of sensor elements and has an electronics chip 1020 positioned below it such that the control electronics for each pixel are positioned directly under the sensor elements. The sensor elements for each detector pixel and the electronics for each detector pixel are bonded together using solder metal bumps 1030.

The electronics elements on the electronics chip 1020 of the hybrid detector 1000 comprise the readout chain including analogue amplification and digital signal conditioning. The output signal from the diode may be amplified by an analogue amplifier and subsequently digitised for one or both of data storage and analysis. The amplified and digitized output signal may be sent to an output unit which may comprise a visual display or communication apparatus such as a network interface for transmitting data indicative of an output of each detector pixel.

Preferably, the sensor chip 1020 and the electronics chip 1010 are as thin as possible. The thickness of both the sensor chip 1020 and the electronics chip 1010 may typically be 50 μm. Other thicknesses of chips 1010, 1020 may be used.

Figure 11:
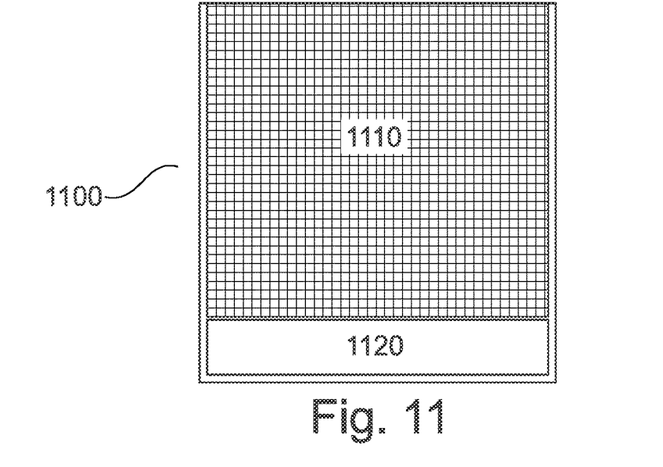
FIG. 11 is a simplified illustration of an example of a monolithic detector for use in the phantom.

Referring to FIG. 11, there is shown another example of a type of detector that may be used as part of the phantom 100. FIG. 11 shows a top view of a monolithic pixel detector 1100, wherein the sensor elements and associated electronics are formed on the same silicon substrate. The detector 140 is made up of pixel matrix 1110 and electronics circuit 1120. In comparison to the hybrid detector 1000 of FIG. 10, the monolithic detector 1100 of FIG. 11 provides the full functionality on the same structure.

Advantageously, the monolithic detector 1100 uses less silicon, as only one thickness of wafer is used instead of two for the hybrid detector 1000. This simplifies the calibration of the energy measurement, that is, the estimate of the energy deposited in water from the measurement in silicon.

The silicon wafers used to form the various detector types typically measure 2 cm×2 cm. Therefore, detectors larger than 2×2 cm$^2$ are made by tiling of a single base unit detector of 2×2 cm$^2$.

Each pixel of the monolithic or hybrid detectors is constituted by a reverse biased diode providing a sensing element for the ionising radiation. The output signal from the diode is amplified by an analogue amplifier and subsequently digitised for data storage and analysis. The amplified and digitized output signal may be sent to the output unit which may comprise the visual display or the network interface. The amplification and digitisation can be called the readout chain. In the hybrid version the readout chain is in the electronics chip and the sensor element on the sensor chip is a reverse biased diode. In the monolithic version the diode, amplifier and some digital function are in each pixels and further digital functions in the periphery of the chip. This is a general scheme that can be implemented with several variants and functionalities.

The detector types have been described as being formed from silicon, however, it will be understood that other suitable materials may be used, such as other semiconductor crystals including Silicon Carbide (SiC), Diamond, Gallium Arsenide (GaAs)

Figure 12:
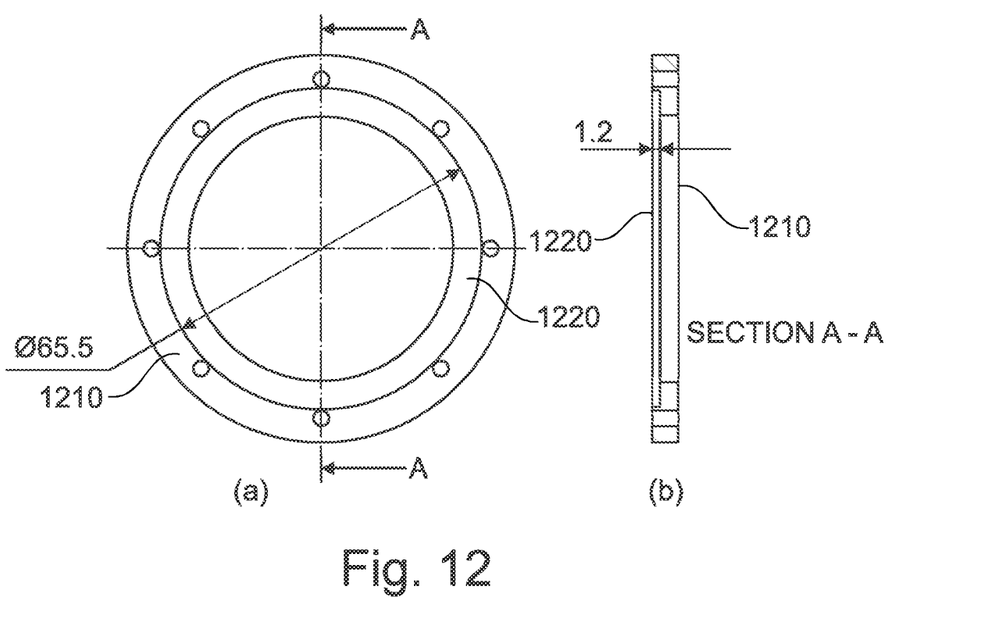

Referring now to FIG. 12, there is shown a circular flange 1210, comprising a lip 1220, for affixing the window 150 over a hole in a wall the vessel 110. The flange 1210 is shown from the front in FIG. 12(*a*), and a cross section A-A of the flange 1210 is shown in FIG. 12(*b*). The flange 1210 has a number of screw holes spaced evenly around it in order to allow it to be attached to a wall of the vessel 110. The lip 1220 forms the inner edge of the flange 1210.

FIG. 12(*a*) shows that the diameter of the lip 1220 is 65.5 mm. As shown in FIG. 12(*b*) the lip 1220 provides a recess having a depth of 1.2 mm around the inner edge of the flange to allow the window 150 to fit under it and be held in place.

Figure 13:
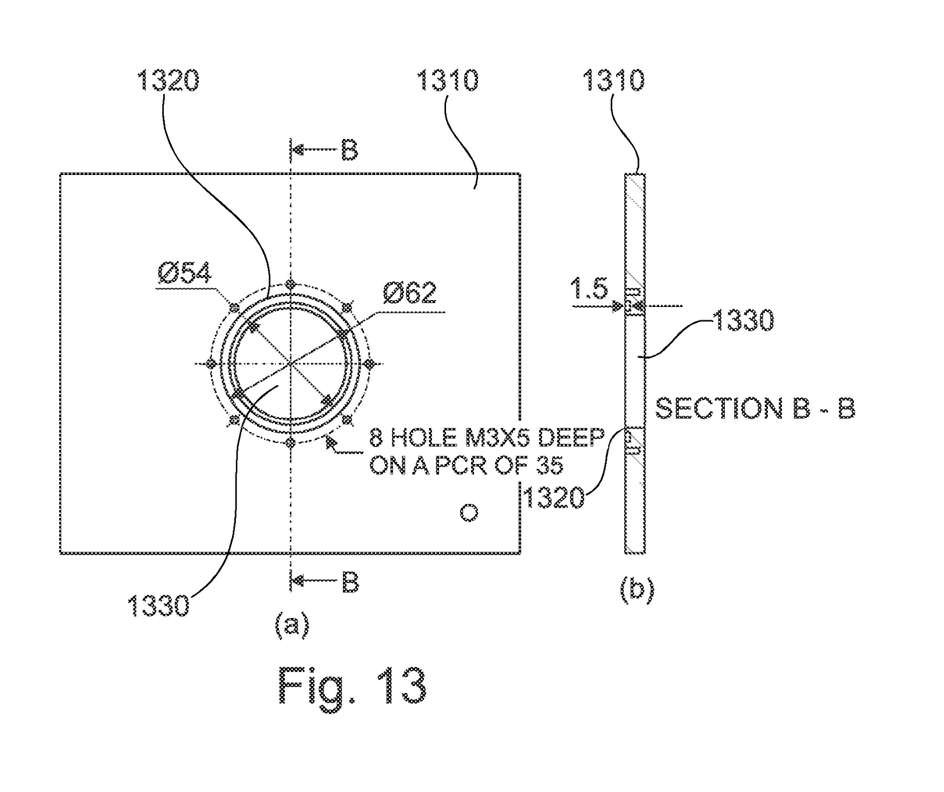

Referring to FIG. 13, there is shown a wall 1310 of the vessel 110 having a circular central through-hole 1330. The central through-hole 1330 is surrounded by an annular channel 1320. The channel may have a depth of 1.5 mm in the wall. The ridge 1320 is a ring, but other suitable shapes may be envisaged. The channel 1320 has an inner diameter of 54 mm and an outer diameter of 62 mm, as labelled in FIG. 13(*a*). The flange 1210 and central through-hole combine support a window in the wall of the vessel. The window is preferably very thin, typically 1.3 mm and is adapted to allow the test radiation beam to pass therethrough.

The window 150 may be held in place by the flange 1210 that may be attached to eight 5 mm deep holes surrounding the window, labelled as "8 HOLE M3×5 DEEP ON A PCR OF 35" in FIG. 13(*a*).

Figure 4:
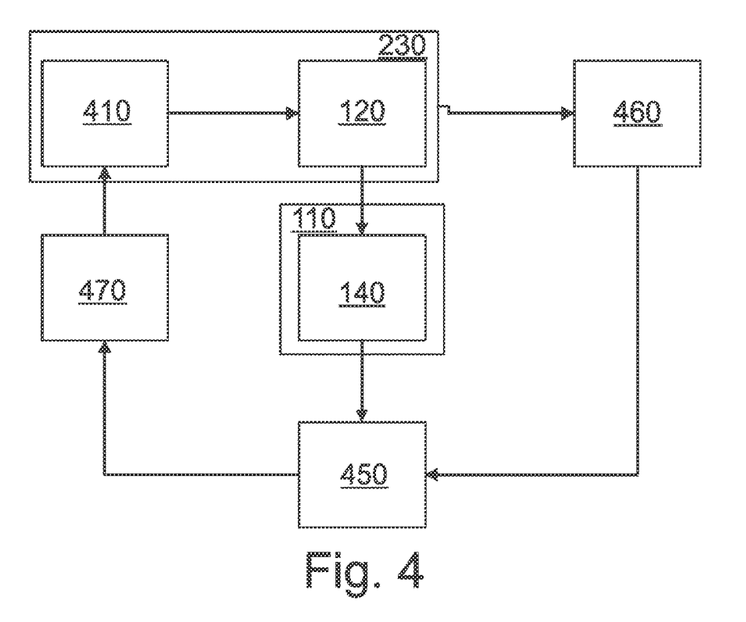
FIG. 4 is a block diagram of an example phantom with a detector inside the vessel.

Referring now to FIG. 4, there is shown a block diagram of the invention with the detector 140 attached to the movable support 230. The movable support comprises the extension arm 120, moved along the linear stage 125 by a motor 410 which is controlled by a controller 470.

The controller 470 is adapted to send an output signal to the movable support 230 to control the position of the detector 140 along the expected path.

A position logging module 460 is used to log the position of the movable support 230 and subsequently the position of the detector 140 inside the vessel 110. The position logging module 460 is adapted to receive an output signal from the movable support 230 detailing the positional information of the detector 140 and thus to log the position of the detector 140 within the vessel 110.

The detector 140 determines the intensity and the measurement of the local energy deposition of the radiation and sends the information gathered to a vector information module 450, which is adapted to receive an output signal from detector 140 and to process information determined by the detector 140. The position logging module 460 may also send positional information to the vector information module 450.

The vector information module 450 may send output signals to the controller 470 detailing the positional and vector information. The controller 470 may then either instruct the motor 410 to move the extension arm 120 further along the linear track 125 or, if the end of the linear track 125 has been reached, instruct the motor 410 to stop and the process to end. The vector information module 450 will process the information in order to determine the range and Bragg peak position of the radiation.

Figure 5:
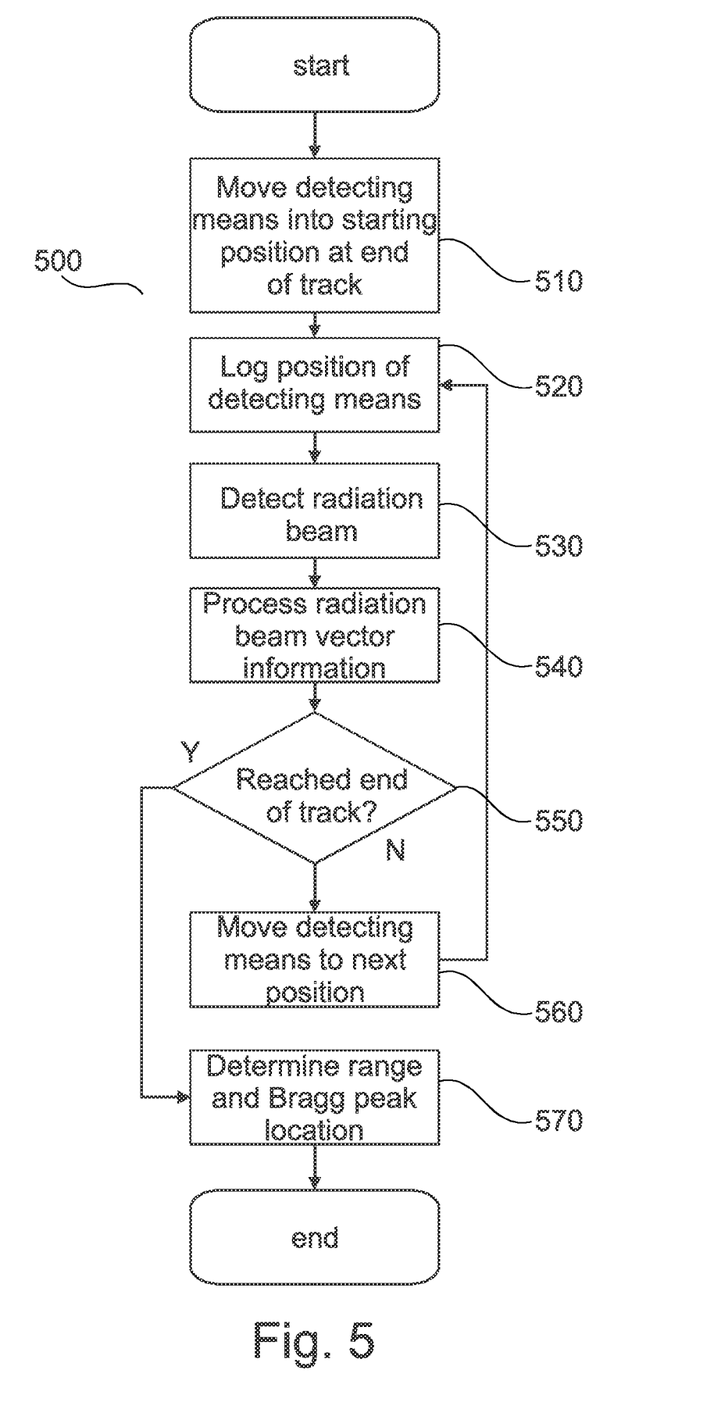
FIG. 5 is a flow chart detailing the process of the phantom and support assembly in use.

Referring now to FIG. 5, there is shown a flow chart detailing a method 500 of operation of the system of FIG. 4. At step 510, the detector 140 is moved into a predetermined starting position. This may be at one end of the stage 195 or at one end of the vessel 110, or any other predetermined position. However, typically the detector starts adjacent the wall through which the test beam enters the vessel. To position the detector in the starting position, the controller 470 sends an output signal to the motor 410 of the linear stage to move the extension arm 120 into the predetermined position.

Next, in step 520 the position of the movable support 230 (and thus the position of the detector 140 within the vessel 110) is logged. The movable support 230 sends an output signal detailing its position to the position logging module 460, which logs the position. The position logging module 460 then sends the positional information to the vector information module 450. The position is logged in order to match a determined intensity of radiation with the position at which it was determined, to help provide a precise three dimensional picture of the radiation.

In step 530, the detector 140 determines the intensity of the radiation in at least two dimensions, perpendicular to the longitudinal axis, simultaneously. Again, this is in order to help provide a precise three dimensional picture of the radiation.

In step 540, the information determined by the detector 140 is sent to the vector information module 450 which then processes the information. The vector information module 450 may determine properties of the radiation such as range in the tissue equivalent liquid, the energy deposition, the intensity and position of the Bragg peak. This is only completed in step 570 after all the information has been gathered and the full three dimensional picture of the radiation can be seen. The determined information is the output to be presented to the user in real time.

In step 550, position logging module 460 determines whether the movable support 230 has reached the end of the linear track 125 and sends an output signal to the controller 470 through the vector information module 450. If the end of the track has not been reached, then the controller 470 instructs the motor 410 to move the extension arm 120 along the linear track 125, and the process continues from step 520 with the extension arm 120, and thus the detector 140, further along the expected path. If the end of the track has been reached, then step 570 is completed—vector information about the radiation is determined by the vector information module 450—and the process ends. Information from the vector information module 450 may be transmitted to a presenting means. The information may be presented to the operators in real time. The information may be stored and presented to the operators at a later time.

Figure 6:
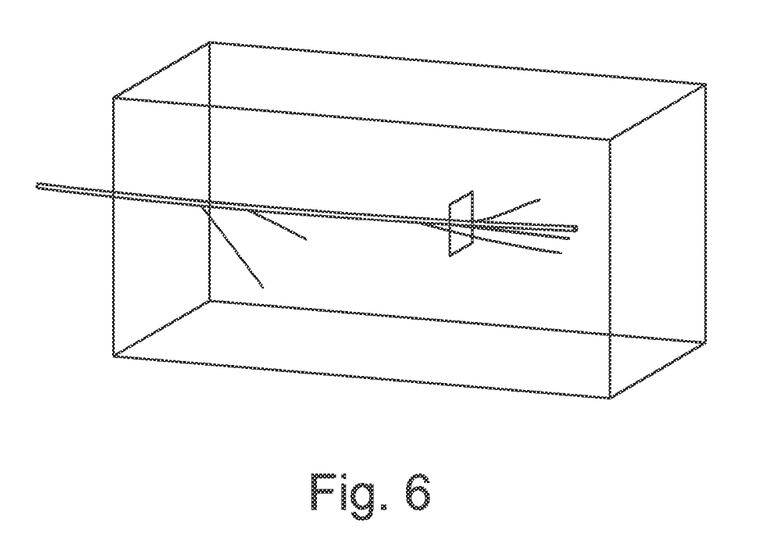
FIG. 6 is an illustration of a simulation of a phantom according to the disclosure, showing radiation beams propagating through the vessel.

Referring now to FIG. 6, there is shown a simulation of the phantom in operation, measuring the intensity at a location along the define path. The lines travelling substantially horizontally represent the beam of test radiation, in this case a proton beam. It can be seen that the beam diverges significantly as it leaves the air and enters the vessel containing the tissue equivalent liquid. The detector is shown perpendicular to the beam, and it can be seen that the path of a number of the protons forming the beam pass through the detector.

It can be seen from this figure how the radiation spreads through the tissue equivalent liquid, propagating towards the detector 140, along the expected path. In this example, the detector 140 would have been moved from the front end of the vessel 110 (the far left of the white box in FIG. 6) toward the back along the expected path in order to determine the intensity of the proton beam in three dimensions.

Figure 7:
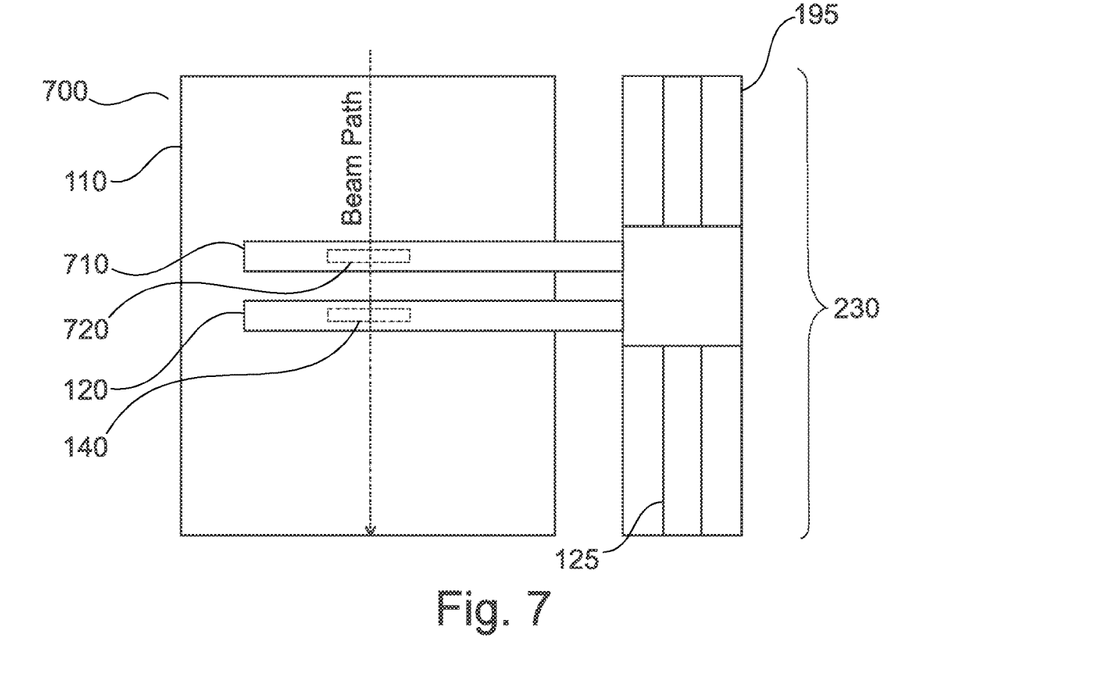
FIG. 7 is a simplified top view of an embodiment of a phantom having two detectors.
Figure 14:
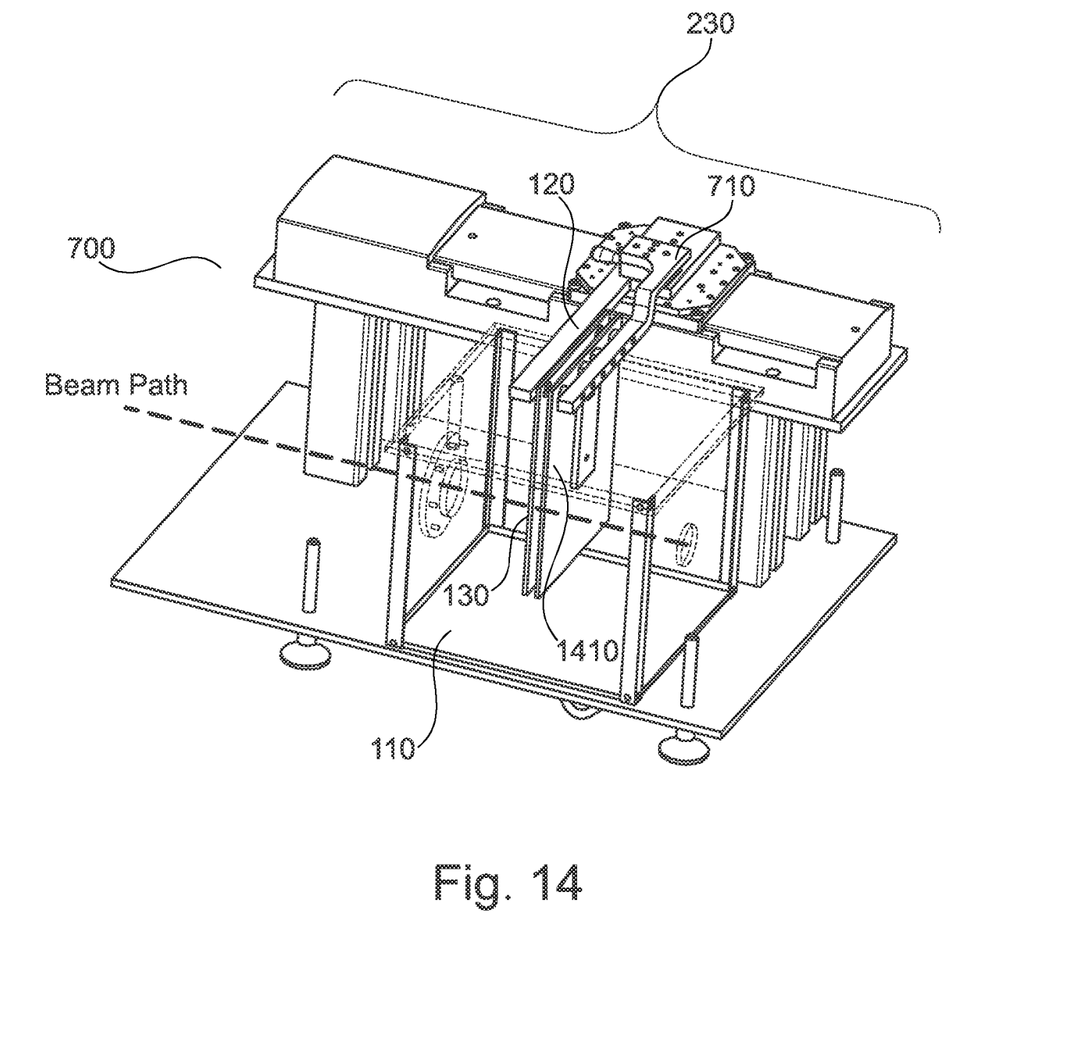
FIG. 14 is a perspective view of an alternative phantom comprising two detectors.
Figure 15:
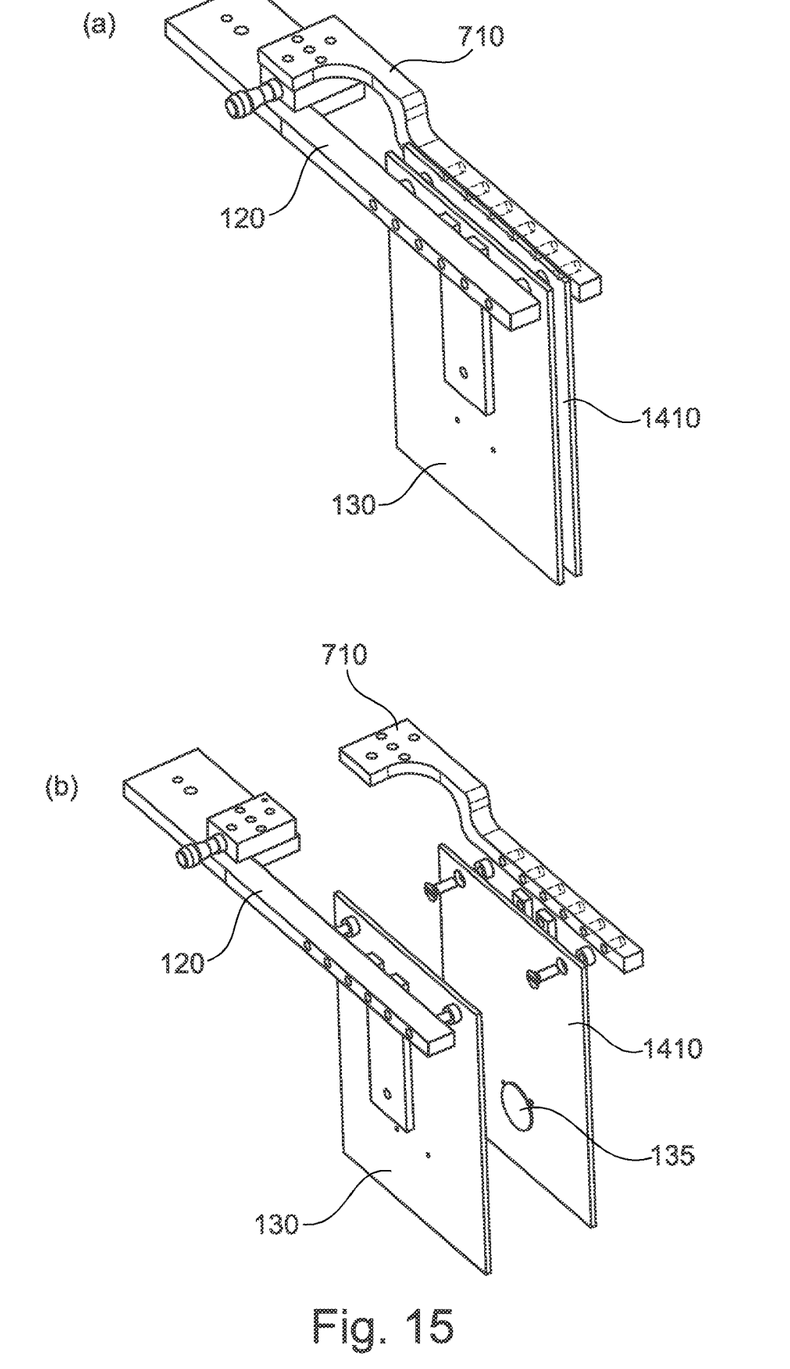

Referring now to FIGS. 7, 14 and 15(*a*) and (*b*), there is shown an alternative phantom, indicated generally by the reference numeral 700, comprising two spaced apart detectors, a first detector 140 and a second detector 720. The phantom 700 is substantially similar to the phantom 100 as shown in FIG. 2, but includes a second detector 720. The second detector 720 is supported in the vessel 110 along the expected path so that the two dimensions of the second detector 720 are substantially perpendicular to the expected path. Thus the second detector is substantially parallel to the first detector 140. The expected path is shown in the figure by a dotted line. As in FIG. 2, the detectors 140, 720 are supported within the vessel by the support assembly.

Two measurements made at different points along the expected path simultaneously, one by each of the first detector 140 and second detector 720, allow the direction and angle of propagation of the radiation entering the vessel to be determined, and provide the local divergence of the beam.

The two detectors 140, 720 may be arranged at a distance from 1 mm to 50 mm from each other. The distance between the two detectors 140, 720 may be adjustable, dependent on the conditions of the test radiation. FIG. 14 shows a micrometer screw to control the separation between the two detectors with high accuracy. If the test radiation is a high energy beam then the detectors may advantageously be spaced further apart. If the test radiation is a low energy beam then the detectors may advantageously be spaced closer together.

The two detectors 140, 720 may be affixed to the same tongue 130 or different tongues 130, 1410. The two detectors 140, 720 may be affixed by PCB holders or other suitable means. Typically, the two detectors are substantially aligned with each other.

FIGS. 14 and 15(*a*) and (*b*) show an arrangement where each detector is affixed to a tongue 130, 1410, in turn mounted on an extension arm 120, 710. Both extension arms are mounted on and controlled by the linear stage.

Figure 8:
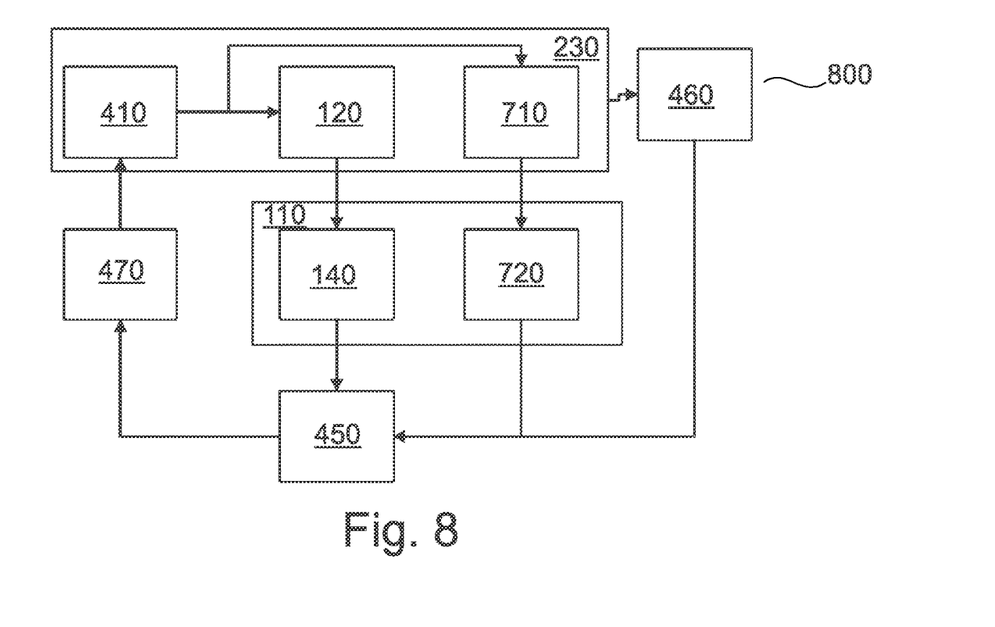
FIG. 8 is a block diagram of an embodiment of the phantom with two detectors.

Referring now to FIG. 8, there is shown a block diagram of an alternative phantom system, comprising the alternative phantom of FIG. 7. In this system 800, both extension arms 120, 710 are moved by the motor 410, which is also part of the movable support 230. The motor 410 is controlled by the controller 470.

Both the first detector 140 and second detector 720 determine the intensity of the radiation and send the information they gathered to a vector information module 450, which acts as a processing means for data gathered by the detector 140, 720. The vector information module 450 is adapted to receive an output signal from the detectors 140, 720 and process information determined by the detectors 140, 720 within the vessel 110. The position logging module 460 may also send positional information to the vector information module 450.

The vector information module 450 may send output signals to the controller 470 detailing the positional and vector information. The controller 470 may then either instruct the motor 410 to move either or both the extension arms 120, 710 further along the linear track 125 or, if the end of the linear track 125 has been reached, instruct the motor 410 to stop and the process to end. The vector information module 450 will process the information in order to determine the range and Bragg peak position of the radiation, as well as the direction and angle of propagation of the radiation.

The beam of test radiation will typically be generated by a radiation therapy device used in the treatment of patients. The phantom may be positioned in relation to the radiation therapy device by a user to simulate the relative positon of a patient to the device when the device is in use for treatment. The radiation therapy device may typically be configured to generate a beam having a substantially round cross section. The beam of radiation may have a full width at half maximum (FWHM) in the range 1 mm up to 2-3 cm. It will be understood that the beam of test radiation generated for use with the phantom will be similar to a beam of therapeutic radiation generated for use with a patient, however the therapy beam may be adjusted based on the output from the detector.

Throughout the description and claims of this specification, the term intensity may be understood to refer to the number of particles in the beam per unit area. Throughout the description and claims, it will be understood that the detector of the phantom may be adapted to determine, in two dimensions, the intensity, the energy deposition or both of the test beam of radiation.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A phantom comprising
   a vessel for containing a tissue equivalent liquid and adapted to pass a beam of test radiation into the vessel,
   a first detector adapted to determine the intensity of the beam of test radiation, the first detector being supported within the vessel and movable therein along an expected path of the beam of test radiation;
   wherein the first detector is a silicon-based 2-dimensional pixel array detector adapted to determine the spatial intensity perpendicular to the expected path of the beam and energy deposition of the beam;
   a second detector collinear with and spaced apart from the first detector, the second detector also being supported within the vessel and movable therein along the expected path of the beam of test radiation in line with the first detector, wherein the second detector is a silicon-based 2-dimensional pixel array detector adapted to determine the spatial intensity perpendicular to the expected path of the beam and energy deposition of the beam.

2. The phantom of claim 1 wherein the vessel comprises at least one wall having a window therein, which window is adapted to pass the beam of test radiation to the tissue equivalent liquid.

3. The phantom of claim 1, wherein the first detector and the second detectors are one of a silicon-based 2-dimensional hybrid pixel array detector, wherein individual pixels are formed by a combination of two semiconductor substrates comprising a sensor substrate having an array of sensor elements and an electronics substrate positioned below the sensor substrate, and a silicon-based 2-dimensional monolithic pixel array detector wherein sensor elements and associated electronics are formed on the same silicon substrate.

4. The phantom of claim 3, wherein in the hybrid pixel array detector the sensor element for each pixel and the control electronics are bonded together using metal bumps.

5. The phantom of claim 1, wherein at least one of the first detector and the second detector is a multi-channel detector.

6. The phantom of claim 1, wherein the vessel contains a tissue equivalent liquid.

7. The phantom of claim 6, wherein the tissue equivalent liquid is water.

8. The phantom of claim 7, wherein the water is deionised water.

9. The phantom of claim 1 wherein the expected path of the beam of test radiation is horizontal.

10. A radiation detection system, comprising the phantom of claim 1; and
    a driven movable support for the detector adapted to move the first and second detectors along the expected path of the beam of test radiation;
    a controller adapted to control the position of the first and second detectors;
    a position logging module adapted to log the position of the first and second detectors within the vessel;
    a vector information module adapted to receive an output signal from the first and second detectors and process information determined by the first and second detectors.

11. A radiation detection system as claimed in claim 10 wherein driven movable support comprises a linear stage.

* * * * *